United States Patent [19]

Maxwell

[11] Patent Number: 5,065,750
[45] Date of Patent: Nov. 19, 1991

[54] MANIPULATIVE SKILL TESTING APPARATUS

[76] Inventor: Robert L. Maxwell, 17777 Palatine Ave. North, Seattle, Wash. 98133

[21] Appl. No.: 511,456

[22] Filed: Apr. 20, 1990

[51] Int. Cl.⁵ ............................................. A61B 13/00
[52] U.S. Cl. ..................................... 128/745; 434/259
[58] Field of Search ..................... 434/256, 221, 224; 128/721, 782, 774, 745; 340/573, 576; 250/221, 570; 377/53, 15, 20, 19

[56] References Cited

U.S. PATENT DOCUMENTS

| 4,009,389 | 2/1977 | Linoholm | 250/221 |
| 4,169,592 | 10/1979 | Hall | 434/258 |
| 4,278,878 | 7/1981 | Kato | 250/221 |
| 4,382,795 | 5/1983 | Collins | 434/258 |
| 4,978,303 | 12/1990 | Lampbell | 434/258 |

Primary Examiner—Kyle L. Howell
Assistant Examiner—Robert L. Nasser, Jr.
Attorney, Agent, or Firm—Jensen & Puntigam

[57] ABSTRACT

A device for testing the manipulative skills of a person suspected of having neurological damage including manipulative devices (6, 16, 18) for measuring small motor skills and a device (10) to record the movement generated.

5 Claims, 2 Drawing Sheets

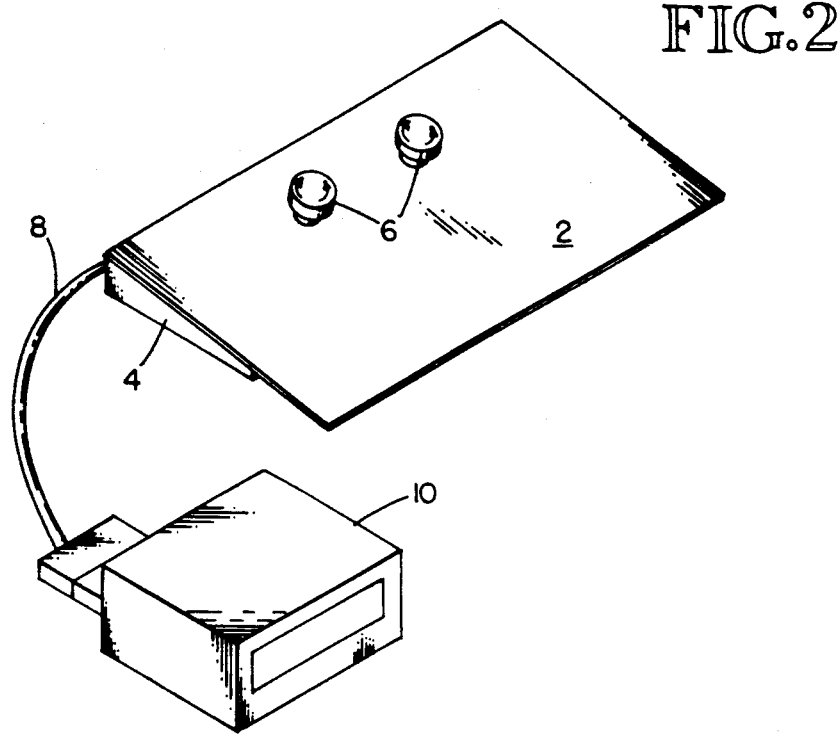
FIG.2
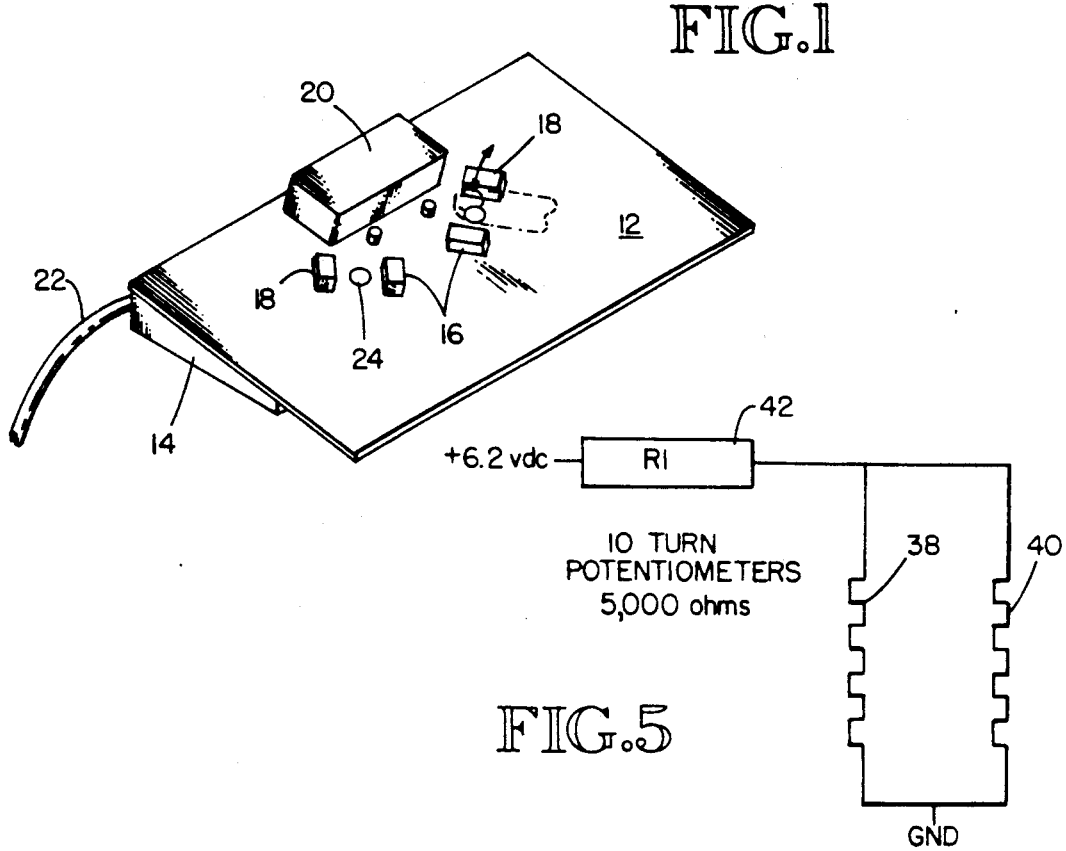
FIG.1
FIG.5

MANIPULATIVE SKILL TESTING APPARATUS

DESCRIPTION

1. Technical Field

This invention relates to apparatus for testing the manipulative skills of those people suspected of having brain dysfunction, neurological disorders or neuropsychological disorders and, more particularly, to a device for measuring and recording the finger-tapping and/or knob-turning capability of the individual.

2. Background Art

Historically, people who are suspected of having brain damage or who have sustained brain damage or, in the alternative, those who have had injuries to the head are tested to determine the extent of brain dysfunction or neurologic damage, if any. Some of the tests which indicate the location of and, to a certain extent, the degree of dysfunction or damage include the testing of manipulative skills, such as repetitive finger movement, foot movement and/or the ability to rotate a knob or the like.

With respect to the ability to administer the finger and/or foot-tapping tests involved the exercise of moving a mechanical device while an observer tabulated the repetition of manipulation as well as the sequence. Obviously this sort of recordation lends itself to those errors inherent with human observation including mistakes and/or oversights caused by fatigue or distractions. Sometimes the physical resistance to movement biased the test against a weak person.

To date there has been no formal neuropsychological test developed for knob turning. However, the development of this test must similarly eliminate human observation inaccuracies as found in the current finger-tapping test.

In order to overcome some of the inadequacies of prior devices, it was determined that the tabulation could conceivably be done electronically and if done electronically, then the physical resistance could be removed enabling a person who is feeble to perform the necessary operations, yielding more accurate results to the test and thus a more complete and accurate diagnosis.

BACKGROUND ART

Prior art other than that described above known to the present inventor, includes U.S. Pat. No. 3,234,512 granted to Burkhart Feb. 8, 1966, which discloses a plurality of light sources and receptors such that communication may be enabled by the appropriate interruption of the light sources.

U.S. Pat. No. 3,764,813 granted to Clement, et al., Oct. 9, 1973, discloses a coordinate detection system wherein a gridwork of intersecting light beams allows the user to determine the location of an object which interrupts the light source.

U.S. Pat. No. 3,775,560 granted to Ebeling et al, Nov. 27, 1973, discloses a crossed light beam positioned in an encoder which includes the provision for sequential scanning.

U.S. Pat. No. 3,955,562 granted Farrar, Jr., May 11, 1975, discloses an apparatus for measuring the range of motion which includes a plurality of mercury switches which are placed in pre-determined locations within the apparatus to be activated by motion of the wearer.

U.S. Pat. No. 4,198,623 granted to Misek et al, Apr. 15, 1980, discloses a touch-entry interactive cathode ray tube arrangement wherein the grid of infrared sources and detectors are non-parallel to more closely follow the curvature of the CRT face and minimize parallax errors.

U.S. Pat. No. 4,424,816 granted to Callahan et al, Jan. 10, 1984, discloses a neurological monitoring device utilizing electrodes placed on the scalp to record brain wave potential. The device includes a circuit for self-testing.

U.S. Pat. No. 4,444,205 granted to Jackson, Apr. 24, 1984, discloses a device including a flexible transducer for assessing joint mobility.

U.S. Pat. No. 4,692,739 granted to Dorn, Sept. 8, 1987, discloses a device utilizing light emitting diodes for input and display of data including a device for controlling sequencing.

U.S. Pat. No. 4,695,827 granted to Beining et al, Sept. 22, 1987, discloses a energy-interference signal for light-beam touch panels.

U.S. Pat. No. 4,703,316 granted to Sherbeck on Oct. 27, 1987, discloses a touch panel including two arrays of light detectors.

U.S. Pat. No. 4,761,637 granted to Lucas et al, Aug. 2, 1988, discloses an infrared touch input system.

U.S. Pat. No. 4,766,425 granted to Tallman et al, Aug. 23, 1988, discloses an oscilloscope capable of displaying a plurality of wave forms and a touch screen method permitting the operator to select a waveform.

U.S. Pat. No. 4,812,833 granted Shimauchi, Mar. 14, 1989, discloses a touch panel input device including an interruptible light beam.

DISCLOSURE OF THE INVENTION

With the above-noted prior art and problems in mind, it is an object of the present invention to provide an easily usable device for testing the manipulative skills of a person suspected of having brain dysfunction or other neurological damage.

It is another object of the present invention to provide an automatic calculator and recorder directly responsive to the manipulative movement providing a valuable research tool.

Still a further object of the present invention is to provide a manipulative testing device that does not provide any or little resistance from the device itself, thus requiring physical strength or stamina to perform the testing.

Yet another object of the present invention is to provide a testing device which is simple and straightforward such that the results are based upon the neurologic health of the individual and not the intelligence.

BRIEF DESCRIPTION OF THE DRAWINGS

FIG. 1 is a pictorial representation of the inventive device as used for finger-tapping.

FIG. 2 is a pictorial representation of the inventive device as used for knob-turning.

FIG. 5 is an electrical schematic for the knob-turning tester.

BEST MODE FOR CARRYING OUT THE INVENTION

Figure 3:
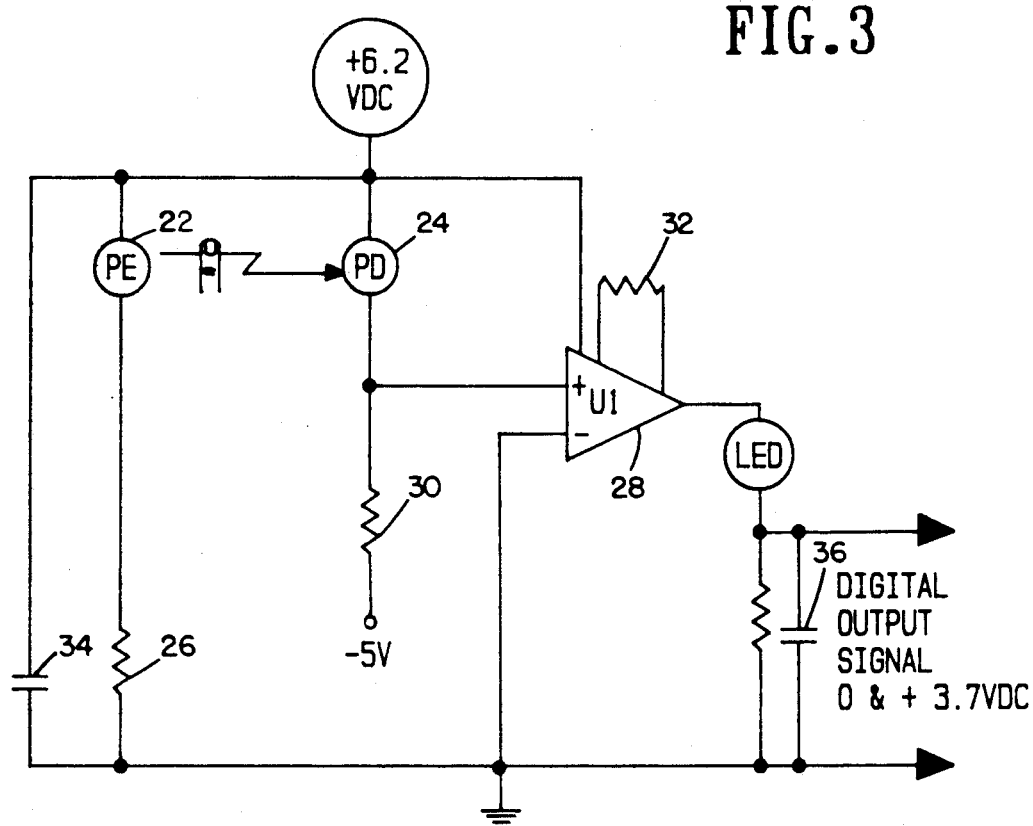
FIG. 3 is an electrical schematic of the finger-tapper or foot-tapper light to digital amplifier.

As seen in Figure the finger-tapper comprises a flat board 12 supported by triangular legs 14 upon which is placed a pair of transmitters 16 and appropriately spaced therefrom are a pair of receivers 18. It is to be understood that the transmitters 16 and the receivers 18 are spaced an appropriate distance apart such that the person being tested may place an index or any other finger between the pair of upstanding interactive pairs thus interrupting the light beam. The equipment also includes an analog to digital converter 20 appropriately interconnected with the signal source, and appropriate electrical circuit 22 such that the results may be transmitted to a computer or other tabulating device.

In operation, the person being tested is requested to place both of his hands flat upon the board 12 with the tip of each of the index fingers resting on a pre-determined spot 24 with the remainder of his hand spread out outside of the sensor area. The operator indicates that the person being tested should begin the test and then begin tapping. The device is capable of being used for single-finger tests and each time the finger interrupts the light beam, the display will increment. When the fingers of both hands are interrupting the light beams, the computer will record every interruption, will increment the count every other interruption for display purposes and the interval between finger taps will be analyzed for constancy and variability.

Referring now to FIG. 3, infrared emitting diode 22 focuses its energy on the photo diode 24 through a self-contained focusing lens. Both of these diodes are located in their own black plastic housing 16 and 18, (see FIG. 1) about 40 millimeters apart. The black color is used to reduce ambient reflections into the diode. The infrared emitting diode 22 is continuously energized with the power turned on by the 6.2VDC power supply from the circuit of FIG. 4 and the current through the emitting diode 22 is controlled by resistor 26. Under the condition that there is no obstruction between the two diodes, the photo diode 24 is in a conducting state. The conduction of the photo diode 24 turns on the operational amplifier by providing a positive voltage to the amplifier 28 which then turns on the light-emitting diode 22 as well as providing a high-level digital output signal. It is to be understood that if the device to be used for more than one appendage, then the circuit will be replicated for each appendage.

Under the condition where there is an obstruction between the two diodes 22 and 24, the light emission supplied by 22 is prevented from reaching 24 and 24 will then significantly reduce its conduction under this condition. Resistor 30 which is connected to a negative supply causes a negative voltage to be provided to the amplifier 28 which turns the operational amplifier off. The light-emitting diode 22 will then be turned off and the digital output signal will drop to a low level.

As a finger goes up and down between the two diodes, the light-emitting diode will go off and on and the digital output signal will go between a high level and low level respectively. Resister 32 limits the gain of the amplifier 28 and prevents oscillation. Capacitors 34 and 36 are to provide further filtering of the power supply, greatly reducing the output signal noise, eliminating false counts.

It is obvious that the finger-tapper and the described circuitry could equally well be modified by placing the black diode holders at about six inches parallel to the front of the panel so that they will be wide enough to allow a foot to fall between them and thus provide a similar response to a foot being moved up and down between the diodes.

Figure 4:
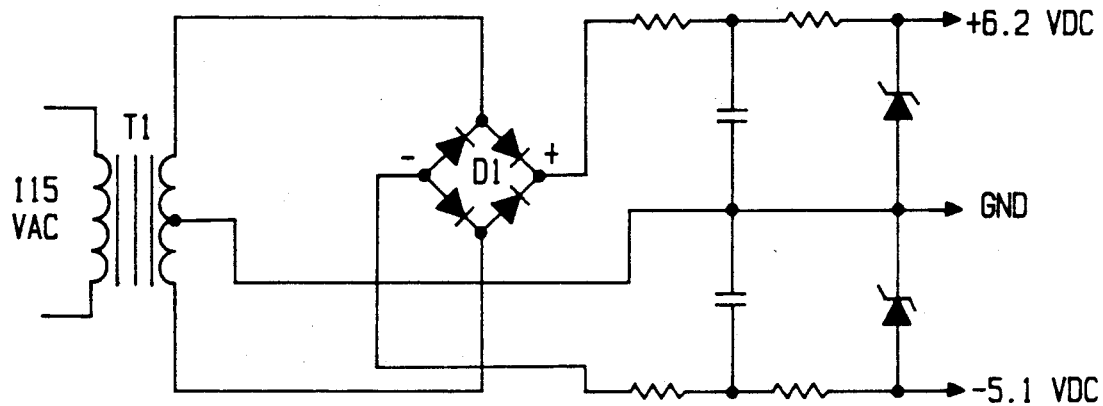
FIG. 4 is an electrical schematic of the power supply for the inventive device.

FIG. 4 is a schematic view of the power supply and is included at this junction for completeness of disclosure and will not be described in detail.

As seen in FIG. 2, the device which is utilized for testing the knob-turning ability and coordination comprises a flat board supported at a slight angle by triangular-shaped legs 4 and including on the upper surface thereof a pair of knurled knobs 6. Knobs 6 include a small spring means or other apparatus to provide a slight resistance to prevent spinning of the knob. As will be explained hereinafter, appropriate electrical connections 8 are provided to transmit the signal generated through an A to D converter as at 10 and to a CRT to display the results of the manipulation of knobs 6. The data will be analyzed for consistency and variability.

Referring now to FIG. 5 which is an electrical schematic which shows a pair of ten-turn potentiometers 38 and 40 and a resister 42 which provides the proper scaling for an analog to digital converter. The equipment as partially described hereinabove includes the knob-turning unit as seen in FIG. 1, an analog to digital converter unit and a computer with which scoring test control and data analysis are performed. The analog to digital converter will accept the analog voltage from both ten-turn potentiometers, convert the voltage to a digital value and send it to the computer for display on the CRT screen for counting and interpretation.

In use, the knob-turning unit is utilized by placing the assembly in front of the test subject. The operator then makes sure that the right-hand knob is turned fully counter-clockwise and the left-hand knob is turned fully clockwise before starting the test. The subject will grasp the right-hand knob with his right hand in a manner such that subsequently he can immediately start turning it clockwise at the operator's signal. When the operator indicates to the patient that he is ready to start the test, he presses the ENTER key on the computer keyboard. The patient immediately starts turning the knob clockwise as fast as he can. The computer will continuously interrogate (approximately 20 times per second) the analog signal and draw a line on the computer display from the bottom of the screen to the top of the screen and display the time it took for the patient to turn the knob completely clockwise. Following the completion of the clockwise turning, the subject will turn the knob counter-clockwise and the line on the CRT will disappear.

When knobs are being turned by both hands, the computer draws two lines on the screen as the knobs are turned. Any variation in how smoothly the knobs are turned or if they are reversed or if they are moved individually will be analyzed for constancy and variability.

Thus, as can be seen, the present invention provides a relatively simple and inexpensive device for not only testing manipulative skills but also because the output permits analysis and tabulation.

I claim:
1. A diagnostic testing device comprising;
platform means for supporting a pair of human appendages whereby the appendage 5 are free to move, means mounted directly to the platform means to generate a signal in response to repetitive movement of each appendage, said means being responsive to the rapidity of movement and sequence of movement during the movement of the appendage, and means to record the signals generated by said movement whereby the respective movements may be analyzed and compared for the determination of brain function.

2. A device as in claim 1 wherein the means mounted directly to the platform means to generate a signal is a light transmitter.

3. A device as in claim 1 specifically designed to measure finger tapping.

4. A device as in claim 1 wherein the means mounted directly to the platform means for generating a signal comprises a transmitter and receiver and the signal between the transmitter and receiver is interrupted by specified body movements.

5. A device as in claim 1 wherein the means mounted directly to the platform means for generating a signal comprises a pair of knobs to be selectively turned.

* * * * *